US006555124B1

(12) United States Patent
Kolter et al.

(10) Patent No.: US 6,555,124 B1
(45) Date of Patent: *Apr. 29, 2003

(54) USE OF (METH)ACRYLIC ACID COPOLYMERS TO INCREASE THE PERMEABILITY OF MUCOUS MEMBRANES

(75) Inventors: Karl Kolter, Limburgerhof (DE); Thomas Subkowski, Mutterstadt (DE); Martin Raditsch, Eppelheim (DE); Volker Schehlmann, Römerberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/230,741
(22) PCT Filed: Jul. 21, 1997
(86) PCT No.: PCT/EP97/03899
§ 371 (c)(1), (2), (4) Date: Feb. 1, 1999
(87) PCT Pub. No.: WO98/05360
PCT Pub. Date: Feb. 12, 1998

(30) Foreign Application Priority Data

Aug. 1, 1996 (DE) .......................... 196 31 084

(51) Int. Cl.[7] .................... A61K 9/14; A61F 13/00
(52) U.S. Cl. .................... 424/434; 424/422; 424/487
(58) Field of Search .................... 424/434, 422

(56) References Cited

U.S. PATENT DOCUMENTS

| 4,003,991 | A | | 1/1977 | Krohn et al. ............... 424/81 |
| 4,704,284 | A | * | 11/1987 | Beatty et al. |
| 4,968,508 | A | * | 11/1990 | Oren et al. |
| 5,376,384 | A | * | 12/1994 | Eichel et al. |
| 5,744,155 | A | * | 4/1998 | Friedman et al. |
| 6,004,575 | A | * | 12/1999 | Luessen et al. |

FOREIGN PATENT DOCUMENTS

| CH | 637017 | 11/1977 |
| EP | 212641 | 3/1987 |
| EP | 266113 | 5/1988 |
| EP | 386688 | 9/1990 |
| EP | 416842 | 3/1991 |
| EP | 417588 | 3/1991 |
| EP | 490305 | 6/1992 |
| EP | 518468 | 12/1992 |
| EP | 544144 | 6/1993 |
| EP | 682945 | 11/1995 |
| GB | 1596166 | 8/1981 |
| WO | 95/15155 | 6/1995 |

OTHER PUBLICATIONS

The American Heritage Dictionary of the Engl8ish Language online, 3rd edition, 1992, Houghton Kifflin Company.*
Eudragit S data sheet, Rohm.*
Eudragit RL/RSD standards sheet, Rohm.*
Umejima etal., *J. of Pharm. Sci*, 84(2), 2/95, 199–202.
Borchard etal., *J. of Cont. Rel.*, 39, 1996, 131–138.
Hochman et al., *J. of Cont. Rel.*, 29, 1994, 253–267.
Holgado et al., *Int. J. Pharm*, 114(1), 1995, 13–21.

* cited by examiner

Primary Examiner—Thurman K. Page
Assistant Examiner—Amy E Pulliam
(74) Attorney, Agent, or Firm—Keil & Weinkauf

(57) ABSTRACT

(Meth)acrylic acid copolymers are used to increase mucosal permeability, comonomers present being (meth)acrylic esters and/or other monomers capable of free-radical polymerization, and the (meth)acrylic acid:comonomer molar ratio varying from 99:1 to 1:99.

8 Claims, 3 Drawing Sheets

USE OF (METH)ACRYLIC ACID COPOLYMERS TO INCREASE THE PERMEABILITY OF MUCOUS MEMBRANES

This application is a 371 of PCT/EP97/03899 filed Jul. 21, 1997.

The present invention relates to the use of (meth)acrylic acid copolymers for increasing mucosal permeability.

Epithelial tissue forms an important permeation barrier to the paracellular transport of hydrophilic active substances, especially those of high molecular weights. What are called "tight junctions" (intercellular junctions between adjacent epithelial cells where the plasma membranes are in direct contact) ensure that the internal environment of an organ is sealed off from the external one. The passive paracellular permeability of these epithelial cells is determined by the tightness of the intercellular contact points. Widening of the "tight junctions" leads to improved absorption and thus to a higher bioavailability of active substances.

Hence there has been no lack of attempts in the past to develop methods for opening intercellular contact points. It has emerged from this that the use of both surface-active ingredients and of $Ca^{2+}$-chelating substances were promising approaches.

However, J. Controlled Rel., 29 (1994) 253 states that on use of surface-active substances there is a risk of cytolysis and, associated with this, toxic side effects.

Numerous publications, inter alia in J. Controlled Rel., 36 (1995) 25; Chem. Pharm. Bull. 33 (1985) 4600; The Journal of Cell Biology, 87 (1980) 736 and Int. J. Pharm., 90 (1993) 229 describe the effect of EDTA or EGTA on the permeability of various cell systems, eg. of caco-2 cells. According to these, the presence of $Ca^{2+}$-chelating substances may lead to rapid, but frequently irreversible, opening of the tight junctions. In addition, in the case of EDTA, relatively high concentrations are required for an effect to be observed (reduction in transepithelial resistance) at neutral pH. In addition, complexing agents with a molecular weight $\leq 20$ kDa are associated with the risk that they undergo systematic absorption and thus may result in unwanted toxic side effects.

It was possible to show, in J. Controlled Rel., 29 (1994) 329, that nonabsorbable high molecular weight compounds based on crosslinked polyacrylates such as polycarbophil (Noveon® AA1, B. F. Goodrich) are likewise able to open tight junctions. There are technical disadvantages on use thereof because of their extremely high molecular weight (>1000 kDa) and their high viscosity even at low concentrations ($\geq 0.5\%$ by weight).

It is furthermore known that polymers with bioadhesive properties are able to improve the bioavailability of active substances. Thus, for example, EP-A-587 047 describes the use of copolymers of (meth)acrylates with various unsaturated carboxylic acids for gestagen-based pharmaceutical compositions.

EP-B-410 422 discloses the possibility of increasing the bioavailability of active substances of low solubility by them being after formulation, owing to the effect of (meth)acrylic acid/(meth)acrylate copolymers, amorphous and thus more soluble.

It is an object of the present invention to find polymers which reversibly increase the permeability of epithelial cells without at the same time having the abovementioned technical disadvantages on use or causing toxicity problems.

We have found that this object is achieved by using (meth)acrylic acid copolymers to increase mucosal permeability and thus enhance the permeation of active substances.

The copolymers according to the invention comprise as monomers acrylic acid or methacrylic acid, which can be employed in the form of their free acid, their salts and/or their anhydrides.

If the monomers are used in the form of their salts for polymerization, the alkaline earth metal, alkali metal or ammonium salts or the salts of organic amines are preferred, and the alkali metal or ammonium salts are particularly preferred.

Further comonomers present are (meth)acrylic acid esters and/or other monomers capable of free-radical polymerization. (Meth)acrylic acid esters of saturated, linear or branched $C_1$–$C_{40}$-alcohols are used. For example methyl, ethyl, n-propyl, i-propyl, n-butyl, i-butyl, tert-butyl, n-hexyl, n-octyl, i-nonyl, n-decyl, n-dodecyl, n-tetradecyl, n-hexadecyl, n-hepta-decyl, n-octadecyl, n-nonadecyl, n-eicosyl, n-docosyl, n-tetra-cosyl, 2-ethylhexyl, i-bornyl acrylate or cyclohexyl acrylate or the corresponding methacrylates. $C_1$–$C_6$- and/or $C_6$–$C_{30}$-alkyl acrylates or methacrylates are preferably employed. Particularly preferred representatives of the group with a $C_1$–$C_6$ chain are methyl methacrylate, ethyl acrylate and butyl acrylate, and $C_8$–$C_{22}$-alkyl (meth)acrylates from the group with a $C_6$–$C_{30}$ chain.

It is also possible to use styrene and/or vinyl esters of saturated $C_1$–$C_{30}$ carboxylic acids as monomer units. Preferred examples thereof are vinyl acetate and/or vinyl propionate.

The (meth)acrylic acid: comonomer molar ratio in the copolymer according to the invention can be varied widely. It is, for example, in the range from 99:1 to 1:99, preferably from 70:30 to 30:70.

The copolymers are normally administered in the form of pharmaceutical compositions together with the active substance. Suitable pharmaceutical forms are tablets, extrudates, granules, pellets, powders, capsules, suppositories, ointments, suspensions or emulsions, it being possible for administration to take place, depending on the application, orally, sublingually, buccally, rectally, through the lungs, nasally or through the mucosa of the eye. Preferred pharmaceutical forms are a) matrix tablets, b) layered tablets and c) film-coated tablets. Matrix tablets in particular, in which the polymer according to the invention and the active substance are intermittently mixed and then compressed together, represent a form with a high activity potential. The content of copolymer to be used according to the invention in these pharmaceutical forms is generally more than 50%, in particular from 60 to 99%, preferably from 75 to 99%, of the total weight of the form. However, it is also possible firstly to treat the mucosa, e.g. of the intestine, throat or eye, with the permeability-increasing copolymer and then to administer the pharmaceutical active substance.

The abovementioned pharmaceutical forms are, as a rule, produced with the addition of bulking agents, binders, disintegrants, lubricants or other ancilliary substances. Bulking agents and dry binders used for tablets are, inter alia, lactose, sucrose, mannitol, sorbitol, microcrystalline cellulose, starch, dicalciumphosphate and polyglycols. Examples of binders suitable for granulation are starch, alginates, polyvinylpyrrolidone and carboxymethyl cellulose. Examples of suitable flow regulators are starch, talc and silicon dioxide. Lubricants which can be used in the mechanical production of tablets are magnesium stearate and other metal soaps. Conventional tablet disintegrants include starch, cellulose derivatives and crosslinked polyvinylpyrrolidone.

Depending on the application and the active substance, the copolymers according to the invention are advantageously used in neutralized, partly neutralized or unneutralized form. If the copolymers are in unneutralized form, it is often advantageous for a base or a proton acceptor, consisting either of another ancillary substance and/or directly of the active substance, to be present.

If the active substance is basic, it can be wholly or partly in salt form with the copolymer according to the invention.

The copolymers are prepared by processes disclosed in the literature, such as solvent polymerization, suspension polymerization or emulsion polymerization, with emulsion polymerization being preferred.

The emulsion polymerization is carried out in a conventional way using initiators such as peroxo or azo compounds, for example dibenzoyl oxide, t-butyl perpivalate, t-butyl per-2-ethylhexanoate, di-t-butyl peroxide, t-butyl hydroperoxide, alkali metal or ammonium persulfates, azobisisobutyronitrile, 2,2'-azo-bis (2-methylbutyronitrile), 2,2'-azobis(2,4-dimethylvalero-nitrile), 1,1'-azobis(1-cyclohexanecarbonitrile), 2,2'-azo-bis (2-amidinopropane) salts, 4,4'-azobis(4-cyanovaleric acid) or 2-(carbamoylazo) isobutyronitrile etc., hydrogen peroxide or redox initiators. The initiators are normally employed in amounts of up to 10, preferably 0.02 to 5, % of the weight of monomers to be polymerized.

The polymerization is carried out in the presence of an emulsifier and/or protective colloid conventional for these purposes. Examples of suitable protective colloids are polyvinyl alcohols, cellulose derivatives or polyvinylpyrrolidones. The emulsifiers can be anionic, cationic or nonionic in nature. Examples of suitable emulsifiers are ethoxylated mono-, di- and trialkylphenols, ethoxylated fatty alcohols or sorbitan esters, alkali metal and ammonium salts of alkyl sulfates or alkyl ether sulfates, of alkylsulfonic acids, of ligninsulfonic acid and of alkylarylsulfonic acids or alkyldiphenyl oxide sulfonates.

The emulsion polymerization normally takes place with exclusion of oxygen at from 20 to 200° C. The polymerization can be carried out batchwise or continuously.

It is preferable to meter at least part of the monomers, initiators and, where appropriate, regulators such as aldehydes, halogen compounds or sulfur compounds, for example formaldehyde, acetaldehyde, bromotrichloromethane, mercaptoethanol, thioglycolic acid or dodecyl mercaptan, at a constant rate into the reaction vessel during the polymerization. The monomers and the initiator can, however, also be initially present and polymerized in the reactor, in which case cooling is necessary where appropriate.

This results in copolymers with a weight average molecular weight of from 50,000 to 2 million. Copolymers with an average molecular eight of from 20,000 to 1,500,000, in particular 120,000 to 400,000, are particularly suitable for their use according to the invention.

Suitable for drying the polymer dispersion are all conventional technologies such as thin-film drying, fluidized bed drying, spray drying or freeze drying.

Figure 1:
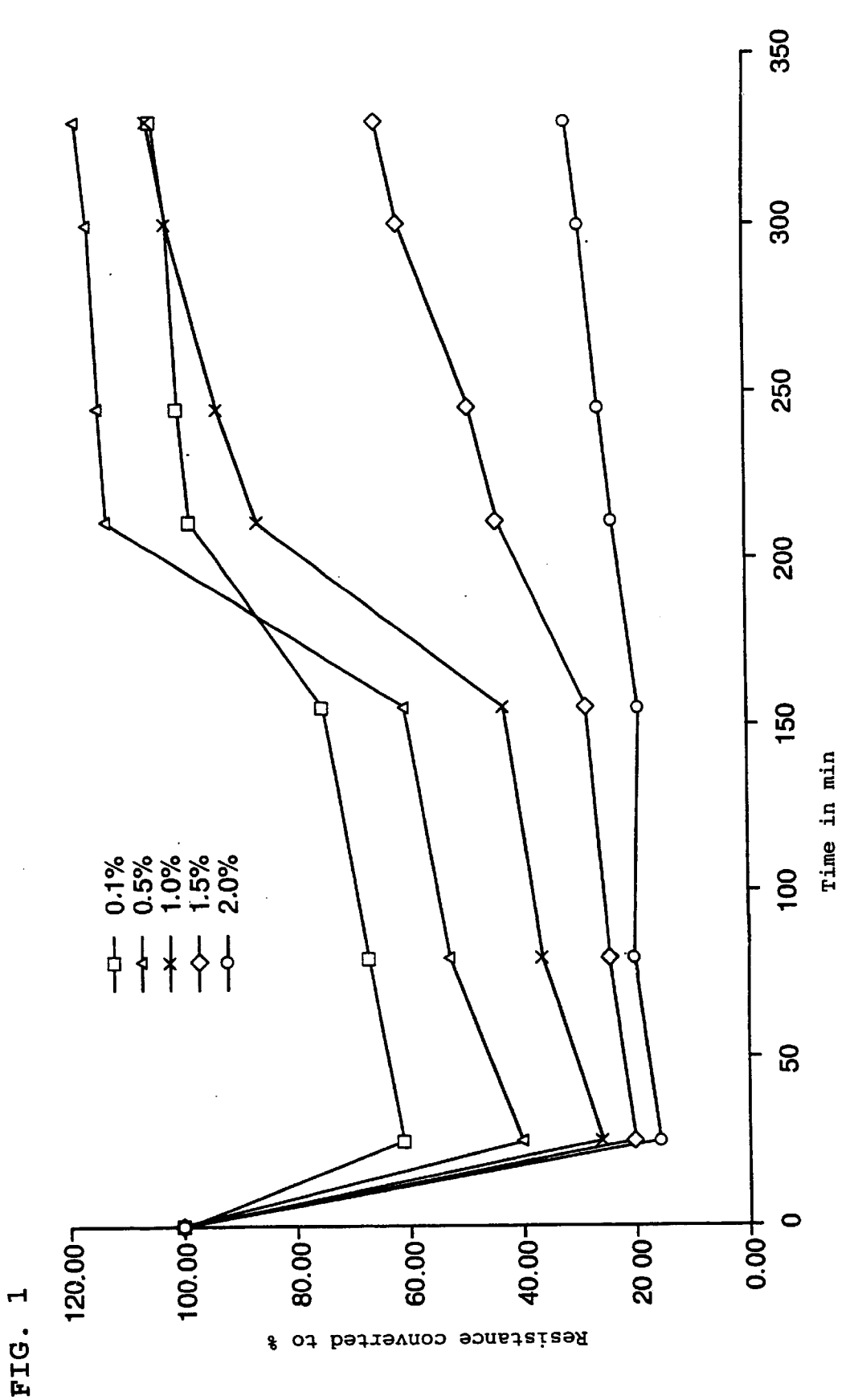
FIGS. 1 to 3 illustrate the effect of representative polymers on the transepithelial electrical resistance (TEER). The specifics of the underlying investigations are provided in Example 3.

The permeability-increasing properties of the polymers to be used according to the invention were demonstrated in an in vitro test system with caco-2 cell cultures (from ATCC, Pockville, Md., USA) as an example. This cell line forms on polycarbonate membranes a tissue assemblage which is very similar in appearance and protein composition to small intestinal endothelium. In the Transwell system (from Costar, Bodenheim, Germany), this artificial endothelial tissue separates two chambers, which are filled with medium, into the apical and the basolateral compartment. This design allows the permeation of a substance through the caco-2 tissue layer to be determined. In this, both the trans-epithelial resistance (TEER) and the permeation of fluorescent tracers [e.g. fluorescein-isothiocyanate-dextran (FITC-dextran-4400; FITC-dextran-11000); fluorescein-biotin=(biotin-amidocaproylamido)-(pentylthioureidyl)-fluorescein] through the cell monolayer indicates how far the tight junctions are opened or closed. An improvement in permeability is indicated by the reversible opening of the tight junctions.

EXPERIMENTAL EXAMPLES

1. Cell Cultivation

Caco-2 cells were cultivated in DMEM (Dulbeccos Modified Eagle's Medium, from Gibco BRL, Eggenstein, Germany) with 10% FCS (fetal calf serum), 1% L-glutamine and 4.5 mg/ml glucose at 37° C. with 5% $CO_2$ and 95% relative humidity. After trypsinization, the cells were spread at a density of $3 \times 10^5$ cells/$cm^2$ on transwell polycarbonate filters. Cells between the 30th and 50th passage were used to form monolayers. The monolayers were employed in the experiment 15–21 days (medium change every three days) after spreading of the cells.

2. Determination of the Permeation Rate

Before the experiment, the caco-2 cell tissue was washed in the Transwell filter inserts with PBS (phosphate buffer saline). Then the apical compartment was filled with EBSS (Earl's buffered salt solution, pH 6) and the basolateral compartment was filled with DMEM. After addition of the polymer to be tested, which had been neutralized to pH 7, [Kollicoat® MAE 30D (ethyl acrylate/methacrylic acid 1:1, BASF), Eudragit® L100 (methacrylic acid/methyl methacrylate 1:1, Röhm), Eudragit® S100 (methacrylic acid/methyl methacrylate 1:2, Röhm)] in a concentration of 0.5–3% by weight and of the tracer substance into the apical compartment, samples were taken after 24 hours, and the permeation rate of the tracer substance was determined.

The experiments were analyzed by fluorescence spectrophotometry (Spex Fluorolog 1680: excitation wavelength: 488 nm, emission wavelength: 513 nm), and in the case of $C_{22}H_{32}N_6O_4$ by HPLC (column material: Vidac C-18; mobile phase: water/acetonitrile/0.1% trifluoroacetic acid; detection: 240 nm), the experimental results are compiled in Table 1. Measurements which were not done have been indicated by "–".

TABLE 1

| Test substance | Kollicoat ® MAE 30 D | | | | |
|---|---|---|---|---|---|
| | Control | 0.5% | 1.0% | 1.5% | 3.0% |
| | Permeation rate [(cm/sec) · $10^{-8}$] | | | | |
| Fluorescein-biotin | 2.3 | 2.3 | 5.8 | 20 | — |
| Dextran-FITC 4400 | 0.8 | — | 9.6 | — | 935 |
| Dextran-FITC 11000 | 2.3 | — | 17.0 | — | 769 |
| $C_{22}H_{32}N_6O_4$ | 56 | 79 | 94 | 280 | — |
| | Eudragit ® L 100 2.0% | | | | |
| | Permeation rate [(cm/sec) · $10^{-8}$] | | | | |
| Fluorescein-biotin | 2.3 | 4.8 | | | |
| $C_{22}H_{32}N_6O_4$ | 56 | 104 | | | |
| | Eudragit ® S 100 2.0% | | | | |
| | Permeation rate [(cm/sec) · $10^{-8}$] | | | | |
| Fluorescein-biotin | 2.3 | 7.1 | | | |
| $C_{22}H_{32}N_6O_4$ | 56 | 103 | | | |

$C_{22}H_{32}N_6O_4$ = HOOC—$CH_2$—(D)-Cha-Pro-NH-3-(6-Am)-Pico

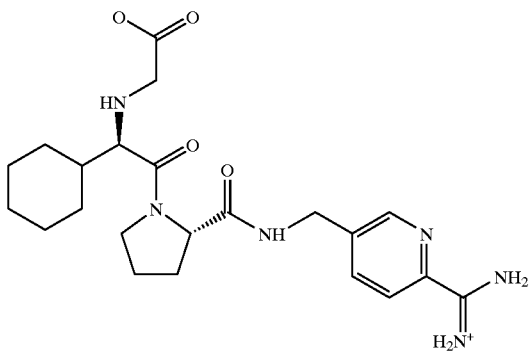

As is evident from Table 1, all three tested polymers showed permeation-enhancing properties. Compared with a control experiment, use of Kollicoate® MAE 30D resulted in a marked increase in permeation even at a concentration of 1% and above.

3. Determination of the Transepithelial Resistance (TEER)

Figure 2:
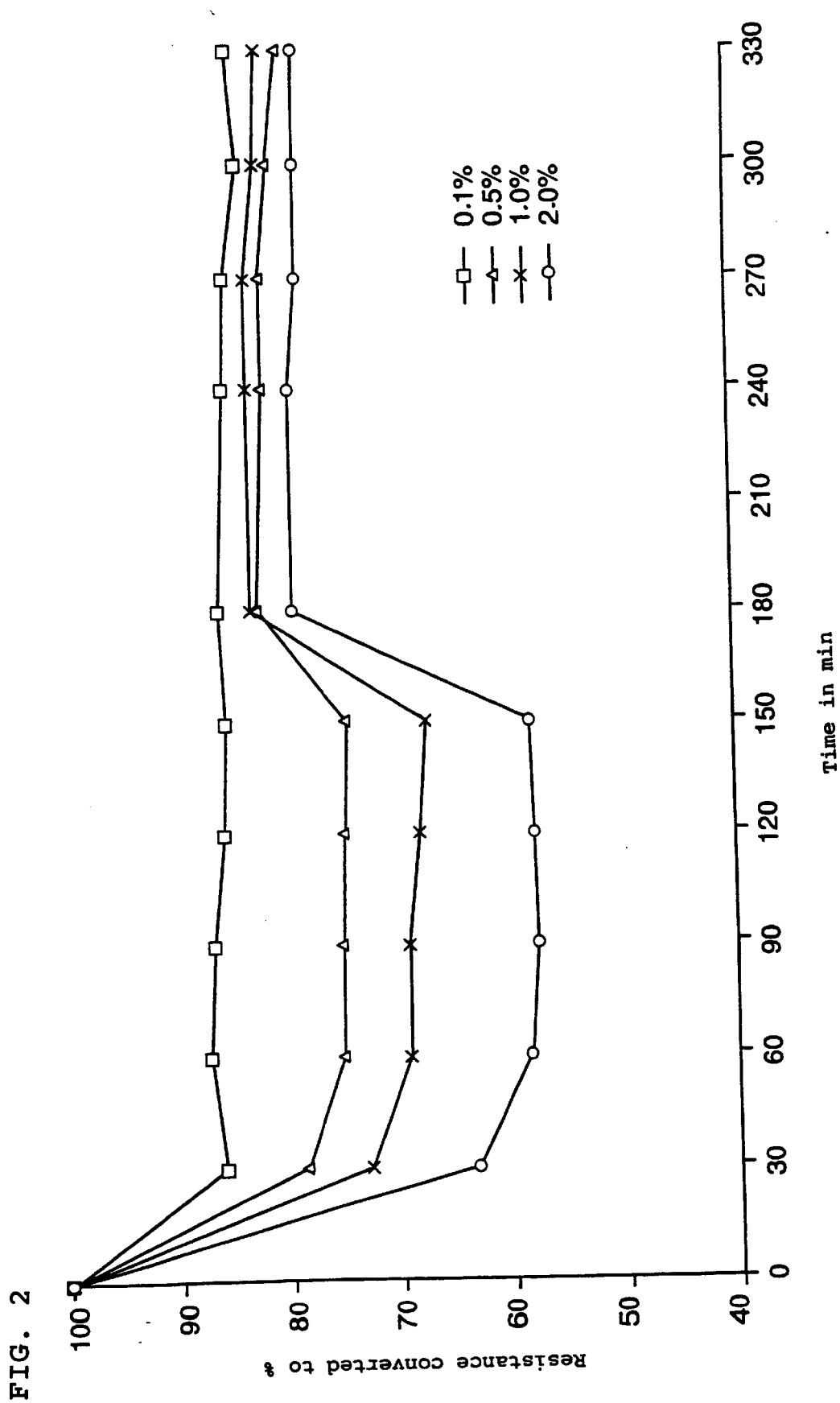
Figure 3:
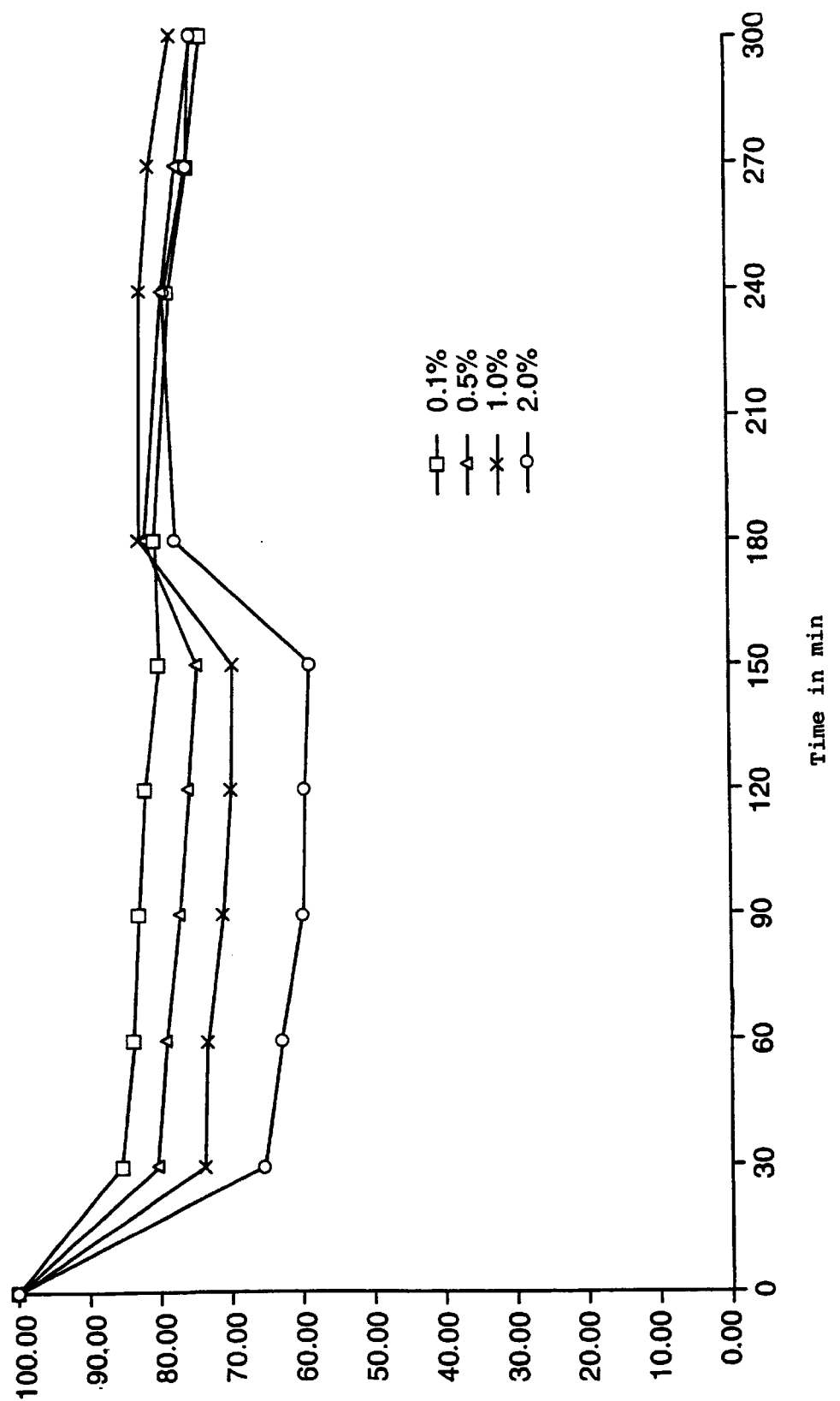

The effect of the polymers according to the invention on the tightness of the tissue (opening of the tight junctions) was determined by measuring the transepithelial electrical resistance. After the caco-2 cell tissue had been washed with PBS, the apical compartment was filled with EBSS (pH 6) and the basolateral compartment was filled with DMEM. The TEER was determined at various times before and after addition of the polymer, which had been neutralized to pH 7, in various concentrations (0.1 to 2%) to the apical compartment (FIG. 1: Kollicoat® MAE 30D; FIG. 2: Eudragit® L100; FIG. 3: Eudragit® S100). After 150 minutes, the solution was replaced by EBSS, pH 6.0, and regeneration of the tissue was investigated on the basis of the TEER.

Both Eudragit® S and L100 and Kollicoat® MAE 30D in particular led to a distinct fall in the measured transepithelial resistance of monolayers of caco-2 cells.

4. Examples of Pharmaceutical Forms
a. Atenolol Film-coated Tablets

| | |
|---|---|
| Atenolol | 50 mg |
| Ludipress ® | 50 mg |
| Methacrylic acid/ethyl acrylate copolymer (1:1), neutralized to pH 7 | 146.5 mg |
| Aerosil 200 ® | 2 mg |
| Magnesium stearate | 1.5 mg |
| Tablet weight | 250 mg |

1000 g of atenolol, 1000 g of Ludipresse® (BASF), 2930 g of methacrylic acid/ethyl acrylate copolymer neutralized to pH 7, 40 g of Aerosil 200® (Degussa) and 30 g of magnesium stearate were initially screened through a 0.8 mm screen and mixed in a Turbula mixer for 5 min. Then biconvex tablets with a diameter of 9 mm were produced in a rotary tablet press under a pressure of 20 kN. A film coating of methacrylic acid/ethyl acrylate copolymer was applied to these biconvex tablets in a horizontal drum coater of the Accela-Cota type (from Manesty) with the inlet air at 50° C. The film-coating dispersion had the following composition:

| | |
|---|---|
| Titanium dioxide | 0.5% by weight |
| Talc | 2% by weight |
| Sicovit ® Red 30 | 0.5% by weight |
| Kollidon ® 30 | 0.5% by weight |
| Methacrylic acid/ethyl acrylate copolymer (1:1), neutralized to pH 7 | 15% by weight |
| Triethyl citrate | 1.5% by weight |
| Water | 80% by weight |

The amount of film-coating dispersion applied to 5000 g of biconvex tablets was 1680.8 g.

b. Propranolol Tablets

| | |
|---|---|
| Propranolol HCl | 160 mg |
| Methacrylic acid/ethyl acrylate copolymer (1:1), neutralized to pH 7 | 190 mg |
| Aerosil 200 ® | 3.4 mg |
| Magnesium stearate | 1.6 mg |
| Tablet weight | 355 mg |

1600 g of propranolol HCl, 1900 g of methacrylic acid/ethyl acrylate copolymer, neutralized to pH 7, 34 g of Aerosil 200® and 16 g of magnesium stearate were initially screened through a 0.8 mm screen and mixed in a Turbula mixer for 5 min. The mixture was compressed in a rotary tablet press of Korsch type PH106 under a pressure of 20 kN at a rate of 30 revolutions per min. Biplanar, bevelled tablets with a diameter of 10 mm and a weight of 355 mg were produced.

c. Furosemide Microtablets

| | |
|---|---|
| Furosemide | 1 mg |
| Methacrylic acid/ethyl acrylate copolymer (1:1), neutralized to pH 7 | 5.95 mg |
| Magnesium stearate | 0.05 mg |
| Tablet weight | 7 mg |

100 g of furosemide and 595 g of methacrylic acid/ethyl acrylate copolymer neutralized to pH 7 were mixed in a Stephan mixer and, while stirring, moistened with 133 g of isopropanol. The moist composition was forced through a screen with a mesh width of 0.6 mm and was dried in a thin layer on a tray at room temperature for 24 h. The dry granules were passed through a 0.8 mm screen and mixed with magnesium stearate, which had likewise been screened, in a Turbula mixer for 5 min and again passed through a 0.8 mm screen. Then biconvex microtablets with a diameter of 2 mm and a height of about 2 mm were produced in a Korsch type EKO eccentric press. For a dose of 40 mg, two-piece gelatine capsules were each packed with 40 microtablets.

d. Methyldopa Tablets

| | |
|---|---|
| Methyldopa | 250 mg |
| Methacrylic acid/ethyl acrylate copolymer (1:1), neutralized to pH 7 | 347.5 mg |
| Aerosil 200 ® | 3.5 mg |

| | |
|---|---|
| Kollidon ® CL | 6 mg |
| Magnesium stearate | 3 mg |
| Tablet weight | 610 mg |

2500 g of methyldopa, 3475 g of methacrylic acid/ethyl acrylate copolymer, 35 g of Aerosil 200, 60 g of Kollidon® CL (BASF) and 30 g of magnesium stearate were initially screened by a 0.8 mm screen and mixed in a Turbula mixer for 5 min. This powder mixture was then compressed to biplanar, bevelled tablets with a diameter of 12 mm in a rotary tablet press under a pressure of 30 kN and at a rate of 30 revolutions per min.

e. S-Adenosylmethionine Pastilles

| | |
|---|---|
| S-Adenosylmethionine | 100 mg |
| Methacrylic acid/ethyl acrylate copolymer (1:1), neutralized to pH 7 | 700 mg |
| Mannitol | 200 mg |
| Aspartame | 3 mg |
| Orange flavor | 5 mg |
| Kollidon ® VA 64 | 37 mg |
| Aerosil 200 ® | 5 mg |
| Magnesium stearate | 5 mg |
| Tablet weight | 1055 mg |

500 g of S-adenosylmethionine, 3500 g of methacrylic acid/ethyl acrylate copolymer neutralized to pH 7, 1000 g of mannitol, 15 g of aspartame, 25 g of orange flavor, 25 g of Aerosil 200 and 185 g of Kollidon® VA 64 were initially screened through a 0.8 mm screen and mixed in a Turbula mixer for 5 min. Then 25 g of magnesium stearate which had previously been screened through a 0.5 mm screen were added and mixed in for 2.5 min. Biplanar, bevelled tablets weighing 1055 mg were produced in a rotary tablet press under a pressure of 35 kN and at a rate of 30 rpm.

f. Cefuroxime Granules

| | |
|---|---|
| Cefuroxime axetil (equivalent to 250 mg cefuroxime) | 300.7 mg |
| Methacrylic acid/ethyl acrylate copolymer (1:1), neutralized to pH 7 | 1250 mg |
| Methacrylic acid/methyl methacrylate copolymer (1:1) | 150 mg |
| Sucrose | 482.3 mg |
| Orange flavor | 5 mg |
| Aspartame | 2 mg |
| Kollidon ® CL | 30 mg |
| Kollidon ® VA 64 | 30 mg |
| Tablet weight | 2250 mg |

300.7 g of cefuroxime axetil (equivalent to 250 g of cefuroxime), 1250 g of methacrylic acid/ethyl acrylate copolymer (1:1), neutralized to pH 7, 150 g of methacrylic acid/methyl methacrylate copolymer (1:1), 482.3 g of sucrose, 5 g of orange flavor, 2 g of aspartame and 30 g of Kollidons® CL were mixed in a Stephan mixer and, while stirring, moistened with a solution of 30 g of Kollidon® VA 64 in 390 g of isopropanol. The moist composition, was forced through a screen with a mesh width of 1.2 mm and was slowly dried on a tray at room temperature for 24 h. The dry granules were packed in sealed closure bags at a dose of 2250 mg.

We claim:

1. A method of reversibly increasing the permeability to active agents of epithelial cells in a patient in need thereof which comprises treating said patient with an effective amount of (meth)acrylic acid copolymers by applying a pharmaceutical composition comprising an amount of more than 50% by weigh, based on the weight of the composition, of the (meth)acrylic acid copolymer, and wherein the pharmaceutical composition is applied orally, sublingually, buccally, rectally, pulmonarily or nasally or through the mucosa of the eye.

2. The method of claim 1, wherein the copolymers comprise in addition to (meth)acrylic acid polymer units, copolymerized units formed from (meth)acrylic acid esters and/or other monomers which undergo free-radical polymerization, and wherein the (meth)acrylic acid polymer units and the copolymerized units are present in a molar ratio of from 99:1 to 1:99.

3. The method of claim 2, wherein the copolymerized units are formed from $C_1$–$C_6$-alkyl (meth)acrylates, styrene, vinyl acetate and/or vinyl propionate.

4. The method of claim 1, wherein the composition comprises the (meth)acrylic acid copolymers in an amount of from 60 to 99% by weight.

5. The method of claim 1, wherein the composition is in form of a tablet, an extrudate, granules, a pellet, a powder, a capsule, a suppository, an ointment, a suspension or an emulsion.

6. The method of claim 1, wherein the copolymers are in unneutralized, partially neutralized or neutralized form, and which, in addition to the copolymers in unneutralized form, optionally further comprises a base or a proton acceptor.

7. The method of claim 1, wherein the composition comprises a basic active substance, said substance being wholly or partly in form of a salt with the copolymer.

8. The method of claim 1, wherein the active agent is a compound of formula

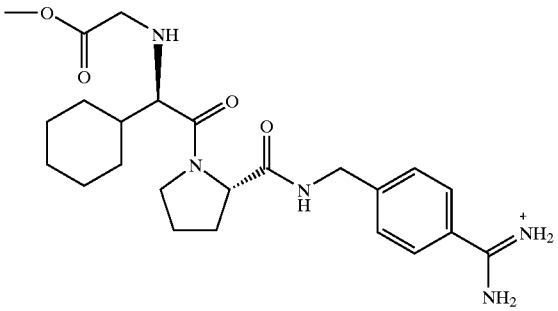

or is fluorescein-biotin, fluorescein-isothiocyanate-dextran, atenolol, propranolol HCl, furosemide, methyldopa, S-adenosylme-thionine or cefuroxime.

* * * * *

UNITED STATES PATENT AND TRADEMARK OFFICE
CERTIFICATE OF CORRECTION

PATENT NO.    : 6,555,124 B1                                                         Page 1 of 1
DATED         : April 29, 2003
INVENTOR(S)   : Kolter et al.

It is certified that error appears in the above-identified patent and that said Letters Patent is hereby corrected as shown below:

<u>Column 8,</u>
Line 11, "weigh" should be -- weight --;
Line 58, "adenosylme-thionine" should be -- adenosylmethionine --.

Signed and Sealed this

Eighth Day of July, 2003

JAMES E. ROGAN
*Director of the United States Patent and Trademark Office*